(12) United States Patent
Wang et al.

(10) Patent No.: US 7,790,469 B2
(45) Date of Patent: Sep. 7, 2010

(54) MICRO STRUCTURE FOR SENSING TRACE CHEMICALS

(75) Inventors: Hong Wang, Cupertino, CA (US); Zhimin Lin, San Jose, CA (US)

(73) Assignee: OptoTrace Technologies, Inc., Mountain View, CA (US)

( * ) Notice: Subject to any disclaimer, the term of this patent is extended or adjusted under 35 U.S.C. 154(b) by 0 days.

(21) Appl. No.: 11/678,053

(22) Filed: Feb. 22, 2007

(65) Prior Publication Data

US 2007/0140900 A1    Jun. 21, 2007

Related U.S. Application Data

(63) Continuation of application No. 10/852,787, filed on May 24, 2004, now Pat. No. 7,384,792.

(51) Int. Cl.
*G01N 21/03* (2006.01)
*G01N 33/553* (2006.01)
*H01L 21/302* (2006.01)
*G01J 3/44* (2006.01)

(52) U.S. Cl. .................. 436/165; 436/525; 438/707; 356/301

(58) Field of Classification Search ............ 436/165, 436/525; 438/707; 356/301
See application file for complete search history.

(56) References Cited

U.S. PATENT DOCUMENTS

| | | | |
|---|---|---|---|
| 5,581,091 A | | 12/1996 | Moskovits |
| 6,017,696 A | * | 1/2000 | Heller .......................... 435/6 |
| 6,139,713 A | * | 10/2000 | Masuda et al. .............. 205/206 |
| 6,214,738 B1 | * | 4/2001 | Aiba et al. .................. 438/707 |
| 6,231,744 B1 | | 5/2001 | Ying |
| 6,464,853 B1 | * | 10/2002 | Iwasaki et al. .............. 205/118 |
| 7,282,446 B2 | * | 10/2007 | Yoo et al. .................... 438/689 |
| 7,428,046 B2 | * | 9/2008 | Wang et al. ................. 356/301 |
| 2003/0175472 A1 | * | 9/2003 | Den et al. ................... 428/66.6 |
| 2003/0186514 A1 | * | 10/2003 | Imada et al. ................ 438/466 |
| 2005/0136552 A1 | * | 6/2005 | Buechler .................... 436/514 |
| 2006/0286684 A1 | * | 12/2006 | Brennan et al. ............. 436/525 |

OTHER PUBLICATIONS

Mardilovich et al., Hybrid Micromachining and Surface Microstructuring of Alumina Ceramic, Electrochemical Society Proceedings vol. 2000-19, pp. 33-42.*

* cited by examiner

*Primary Examiner*—Lore Jarrett
(74) *Attorney, Agent, or Firm*—Xin Wen

(57) ABSTRACT

A method to fabricate an optical scattering probe and the method includes the steps of a) depositing an conductive layer on a substrate followed by depositing a noble metal layer on top of the conductive layer and then an aluminum layer on top the noble metal layer; b) anodizing the aluminum layer to form a porous aluminum oxide layer having a plurality of pores; and c) etching the plurality of pores through the aluminum oxide layer and the noble metal layer for forming a nano-hole array. In a preferred embodiment, the step of etching the plurality of pores through the aluminum oxide layer and the noble metal layer further comprising a step of widening the pores followed by removing the aluminum oxide layer for forming a plurality of noble metal column on top of the conductive layer.

40 Claims, 6 Drawing Sheets

SECTION A-A

MICRO STRUCTURE FOR SENSING TRACE CHEMICALS

The present patent application is a continuation patent application and claims priority to commonly assigned U.S. patent application Ser. No. 10/852,787, entitled "Method of fabricating nano-structured surface and configuration of surface enhanced light scattering probe", filed May 24, 2004, now U.S. Pat. No. 7,384,792 the disclosure of which is incorporated herein by reference.

BACKGROUND OF THE INVENTION

1. Field of the Invention

This invention relates generally to the methods and systems for detection of very small amount of trace chemicals by employing light scattering probes. More particularly, this invention relates to an improved light scattering probes and detection system based on a novel process to fabricate a sensing chip with nano-structured noble metal surface with improved configurations to detect the trace chemicals with significantly improved detection sensitivity.

2. Description of the Prior Art

Historically, one of major limitations of Raman spectroscopy application is the weak Raman scattering signals for trace chemical detection. It is known in the art that there is a potential solution by employing roughened or the nano-structured sensing surface to generate scattering signals of higher intensity. Specifically, the nano-structured materials have found numerous applications in sensing, bioscience, materials science, semiconductor, etc. One of the promising applications of sensing technologies with nano-structured materials is Surface Enhanced Raman Spectroscopy (SERS) and Surface Enhanced Resonance Raman Spectroscopy (SERRS). It has been discovered that the Raman scattering, signal can be enhanced by $10^4 \sim 10^{14}$ times when molecules are adsorbed on a nano-structured noble metal (such as Ag and Au, but not limited to Ag and Au) surface compared to normal Raman scattering. Specially, Raman scattering signal gets remarkably enhanced if the surface nanoparticles are isolated. The enhancement is determined by several factors, among them, the dimensions of the nano-particles and the distance among these nanoparticles on the surface are very important. It is found that as the scale of these nanoparticles decreases, the signal enhancement of Raman scattering increases. Further, as the distance between neighboring nano-particles islands varies, the enhancement effect of Raman scattering also varies. However, the conventional technologies, for example, VLSI lithography technology, are still encountered with technical difficulties to fabricate nano-structure surfaces with reduced dimensions of the nano-particles and reduced distance among these nano-particles on the surface to achieve scattering signal enhancement.

The very limited availability of non-contaminated nano-structured noble metal surface is still a major difficulty faced by those of ordinary skill of the art in applying the technologies of Surface Enhanced Raman Scattering (SERS) and Surface Enhanced Resonant Raman Scattering (SERRS) for trace chemical detection. A non-contaminated nano-structured noble metal surface is required to conveniently deploy in the field for molecular adsorption and subsequent measurement. Due to this limit availability, even though the detection of trace chemicals can be achieved a part-per-billion (ppb) level, the techniques of applying SERS and SERRS for detecting trace of explosives and/or other chemical materials still have very limited applications.

The technologies of applying SERS and SERRS for detecting trace chemicals were described in many published papers such as "Probing Single Molecules And Single Nanoparticles by Surface Enhanced Raman Scattering", Shuming Nie and Steven R. Emory, Scince, 1997, 275, 1102-1106; "Surface Enhanced Raman Spectroscopy of Individual Rhodamine 6G Molecules on Large Ag Nanocrystals", Amy M Michaels, M. Nirmal, and L. E. Brus. J. Am. Chem Soc. 1999, 121, 9932-9939; "Single Molecule Detection Using Surface-Enhanced Ramam Scattering (SERS)", Katrin Kneipp, Yang Wang, Harald Kneipp, Lev L. Perelman, Irving Itzkan, Physical Review Letter, 78, 1997. 1667-1670; "Nanosphere Lithography: A versatile Nanofabrication Tool for Studies of Size-Dependent Nanoparticle Optics", Christy L. Haynes and Richard P. Van Duyne, J. Phys. Chem. B 2001, 105, 5599-5611.

However, these publications do not provide an effective method to produce and package the non-contaminated nano-structured noble metal surface to achieve field applications of SERS and SERRS for trace chemical detection. Furthermore, none of these publications provide method to fabricate nano-structured materials with well-controlled nano array that have reduced and optimized dimensions of the nano-particles and reduced and optimized distances among these nano-particles on the surface to achieve scattering signal enhancement.

Therefore, a need still exists in the art of design and manufacture of optical probes for trace chemical detection by providing new and improved methods to fabricate nano-structured materials with Raman scattering signal-enhancing surfaces and improved detector configuration for packaging and deploy the optical probes such that the above discussed difficulties and limitations can be resolved.

SUMMARY OF THE PRESENT INVENTION

It is therefore an object of the present invention to provide a new design of SERS and SERRS optical sensors that are suitable for portable applications. In particular, the invention is an optical sensor designed to provide ultra sensitive trace chemical detection. The sensor incorporates a nano-structured flexible noble metal surface that can be rolled onto a roller, a mechanism to protect the nano-structured surface from contamination, a method to enhance the surface adsorption by applying positive or negative voltage on the sensing surface, and a mechanism to expose a small portion of the surface for SERS or SERRS measurement.

An object of this invention is to provide a method and process for producing nano-structured noble metal surfaces. In particular, the invention describes a technology and a fabrication process for producing well-controlled self-assembled nano-structured surfaces with scales down to few nanometers. Such nano-structured surfaces are critical for SERS and SERRS application. Furthermore, the present invention provides a method of producing the nano-structured surface on a flexible substrate for field SERS and SERRS application. The nano-structured metal surface is prepared on a Si (100) surface or other material that has the similar structure and purity to minimize unwanted contaminations. Raman scattering band at 520 $cm^{-1}$ from silicon crystalline substrate's Si (100) surface can be used as the internal frequency and intensity reference in SERS and SERRS field application. A conductive metal layer, such as titanium (Ti), nickel (Ni), is deposited between silicon substrate and nano-structured noble metal surface. A positive or negative voltage can be applied to the nano-structured sensing surface through the conductive metal layer to attract electrically charged anions or cations of interest. One can also apply lower temperature (lower than room temperature) to nanostructured sensing surface through the conductive metal layer to attract trace chemicals of interest. Metal film deposition, anodization, oxide etching, and chemical mechanical polishing (CMP) processes are used to create noble metal rods on a Si (100) surface covered with a conducting metal layer. The size of the noble metal rods and the interspacing between the rods can be determined by controlling anodization process steps. The height of the noble metal rods can be controlled by thin film deposition and chemical etch processes. The rods can be fabricated with the diameter size as small as 5 nm. Once the nano-surface structure is created, the chips can be diced into small pieces and sealed for field applications. Detailed description of nano-structured surface material packaging will be described in a separate invention disclosure.

It is another object of this invention to provide the nano-structured noble metal surface with encapsulated in a protective thin film with pocket size partitions. Each pocket is sealed and separated from each other. The thin film can be removed one pocket at a time to allow a fresh nano-structured surface to be exposed to trace molecules. The metal surface is connected to a DC voltage source for applying a positive or negative voltage on the surface to enhance the molecular adsorption. Further, the nano-structured noble metal surface with protective thin film is in a cell that has optical windows to allow a laser beam to enter and scattering light to exit. The cell has two hoses. One is connected to a micro-pump and the other is connected to ambient. There are two valves to control the airflow through the cell. The beam delivery optics directs the focused laser beam towards the nano-structured surface. The imaging and dispensing optics collects and spectrally separates the scattered light and subsequently image the scattered light to a two-dimensional CCD camera. The image acquisition and process hardware and software processes the spectral image and compare the spectral distribution to a database to determine the adsorbed molecules on the nano-structured noble metal surface. The nano-structured noble metal surface is normally protected with a thin film material to keep the surface clean and contamination free. The nano-structured surface is partitioned into pocket cells that are air tight sealed with a thin film covering over the pocket cells. The nano-structured surface is packaged into a roller and is pulled through another roller. The entire package is encapsulated with a probe cell that has hoses connected to a vacuum pump and valves to allow sample molecules intake. Once the sample molecules are pumped into the probe cell, the probe cell is sealed with both the molecule intake valve and vacuum pump valve. The pulling roller is then advanced by on pocket cell length to remove the thin film that covers the sealed nano-structure surface and expose the surface to sample molecules. A rolling mechanism is incorporated into the cell to expose a small portion of the surface after the cell is filled with fresh sample (air) for measurement.

Briefly, in a preferred embodiment, the present invention discloses a method for fabricating, an optical scattering probe. The method includes the steps of a) depositing a conductive layer on a substrate followed by depositing a noble metal layer on top of the conductive layer and then an aluminum layer on top the noble metal layer; b) anodizing the aluminum layer to form a porous aluminum oxide layer having a plurality of pores; and c) etching the plurality of pores through the aluminum oxide layer and the noble metal layer for forming a nano-hole array. In a preferred embodiment, the step of etching the plurality of pores through the aluminum oxide layer and the noble metal layer further comprising a step of widening the pores followed by removing the aluminum oxide layer for forming a plurality of noble metal column on top of the conductive layer. In another preferred embodiment, the step of depositing the conductive layer on the substrate is a step of depositing a titanium layer. In a preferred embodiment, the step of depositing the aluminum layer on top of the noble metal layer is a step of depositing an aluminum layer with a purity of about 99.999%. In a preferred embodiment, the step of depositing the conductive layer on the substrate is a step of depositing a titanium layer having a thickness of about one hundred to one thousand Angstroms. In another preferred embodiment, the step of depositing the aluminum layer on top of the noble metal layer is a step of depositing an aluminum layer having a thickness of about one to ten micrometers. In a preferred embodiment, the method further include a step of packaging the substrate supporting the plurality of noble metal columns into a trace chemical detecting chip, e.g., RamanNanoChip™, and place the chip into an air tight probe cell. In another preferred embodiment, the method further includes a step of placing an array of the trace-chemical detecting chips into a moveable surface for sequentially applying each of the detecting chips as the key part of an optical scattering sensor, e.g., RamanSensor™

This invention discloses a method for forming a nano-structure includes a step of applying an anodization process for forming a porous layer having a plurality of holes followed by etching a plurality of nano-holes. The method further includes a step of filling the nano-holes with a nano-column material followed by removing the porous layer for forming a plurality of nano-columns. In a different embodiment, the method includes a step of forming the porous layer on top of a layer composed of a nano-column material followed by etching and widening the nano-holes to form a plurality of nano-rod array.

These and other objects and advantages of the present invention will no doubt become obvious to those of ordinary skill in the art after having read the following detailed description of the preferred embodiment, which is illustrated in the various drawing figures.

BRIEF DESCRIPTION OF THE DRAWINGS

FIG. 7G is a cross sectional view along line AA in FIG. 7E. FIG. 7I is a cross sectional view along line BB in FIG. 7H.

DETAILED DESCRIPTION OF THE PREFERRED EMBODIMENT

Figure 1:
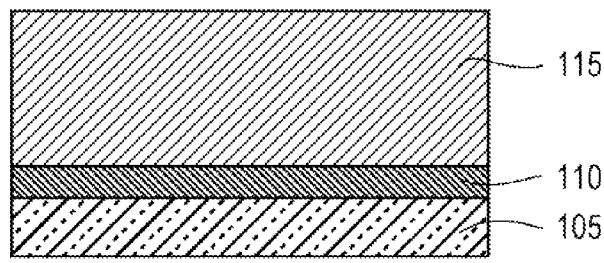
FIG. 1 is a cross sectional view of a three layer structure to start the process for fabricating a nano-structured surface.
Figure 2B:
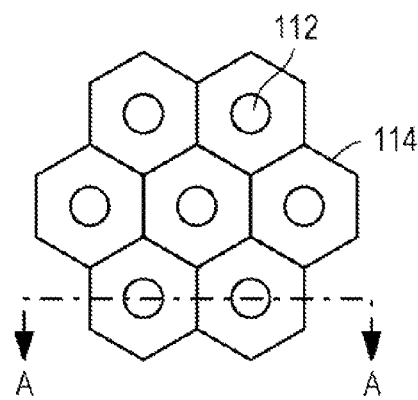
FIGS. 2A to 2C are respectively a cross sectional view of an assisting layer with holes formed by anodization process, a top view and a side cross sectional view along a horizontal one over the top view of FIG. 2B.
Figure 2A:
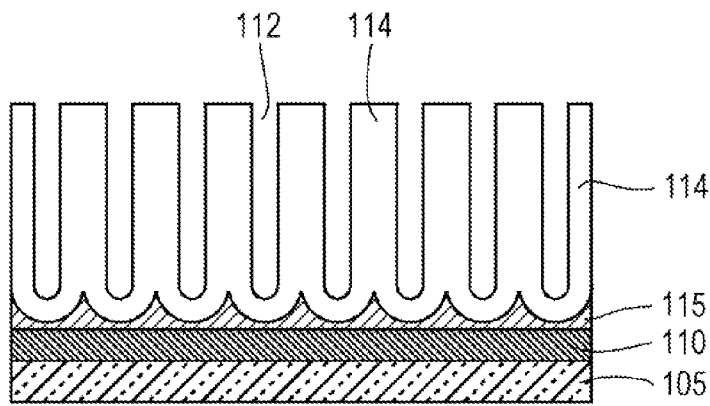
Figure 2C:
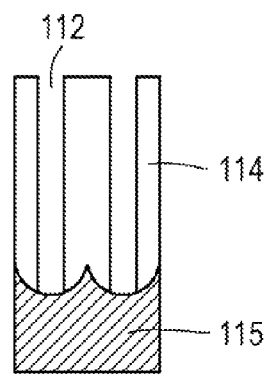
Figure 3:
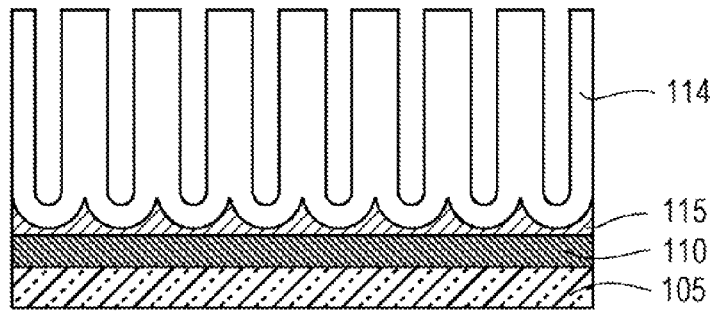
FIG. 3 shows a cross sectional view of the nano-structured surface after performing a wet chemical etch or CMP process.
Figure 4:
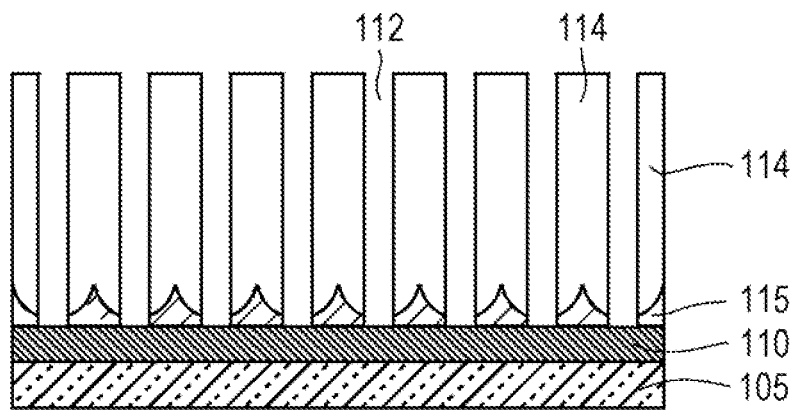
FIG. 4 shows a cross sectional view of the nano-structure surface after removing the barrier layer at the bottom of the holes and etching down to the conducting layer by applying an oxide etching.

Referring to FIGS. 1 to 6 for a series of processing steps to fabricate a nano-structured noble metal surface of this invention, FIG. 1 shows a two-layer structure with n-type silicon (100) flat wafer (3-8 Ω-cm) or oxidized (30-50 nm $SiO_2$) type silicon (100) flat wafers (5-10 mΩ-cm), an electrically and thermally conductive layer 110 deposited on a silicon (100) substrate 105. The thickness of the conductive layer 110, such as Ti and Ni, is optimized to provide i) best adhesion to a subsequently deposited noble metal film, such as Ag, or Au film, etc., ii) electrical conductive film to apply electrical bias to sensing surface in field application, iii) thermal conductive layer to apply lower temperature of sensing surface. The thickness of this metal film is usually controlled in the range of 100 Å-1,000 Å. Then an aluminum layer 115 with purity of 99.999% and thickness in the range of 1.0-10.0 μm is deposited on top of the conductive layer 110. Prior to anodization, silicon wafers with Ti conductive layer and Al layer are annealed at 400° C.-500° C. in a $N_2$ purged furnace for 2-5 hours to recrystallize the Al film. An anodization process is performed to produce a porous structure in a form of porous aluminum oxide layer 115 as that shown in FIG. 2A. FIG. 2B is a top view of the porous structure formed on the aluminum oxide layer 115 wherein the porous structure includes a plurality of pores 112 surrounded by pore wall 114 with the cross section view along a horizontal line A-A shown in FIG. 2C. Then wet oxide etch process is carried out in FIG. 3 to remove both top porous $Al_2O_3$ layer and barrier layer. A second anodization process is carried out to consume all Al metal so that the barrier layer and top porous $Al_2O_3$ layer are right above the conductive metal layer. In FIG. 4, an oxide etching is carried out to remove the barrier layer at the bottom of the pores and to widen the pore diameter. After the completion of the wet etch process, the pores 112 are extended downward to reach the conductive layer. The thickness of the resulted porous oxide layer can be controlled by controlling the processing parameters of aluminum physical vapor deposition (PVD); anodization and the subsequent wet etch processes. The self-assembled pore structure is naturally formed with a hexagonal array. The pore diameter (d) depends on applied anodization voltage (V), current density (i) and electrolyte, and the subsequent pore widening wet etch process; while the inter-pore distance (D) depends on applied anodization V, i and electrolyte.

Figure 5A:
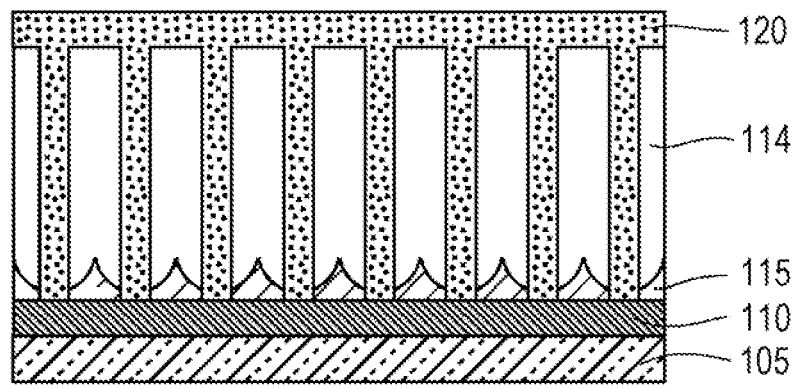
FIGS. 5A and 5B show respectively a noble metal deposited on top of the nano-structured surface then followed by removing the noble metal film from the top layer.
Figure 5B:
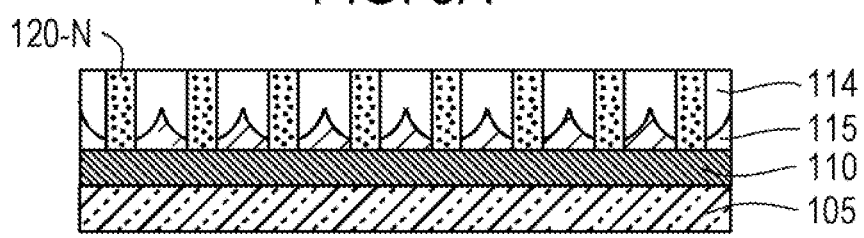
Figure 6:
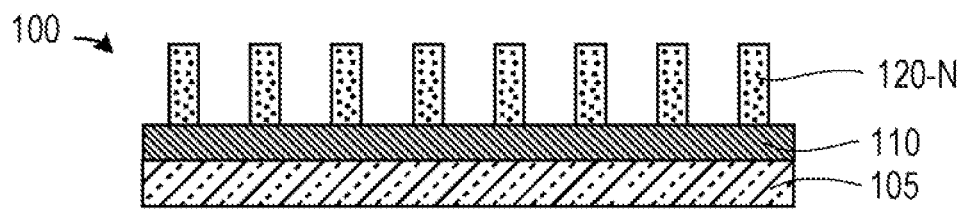
FIG. 6 shows the side cross sectional view of the nano-structured surface with noble metal rods after the oxide layer is removed.

A noble metal, e.g., Ag layer 120 is deposited on top of the porous layer 115 in FIG. 5A and filling the pores 112 by bias PVD process or plating method. In FIG. 5B, the top layer of the noble metal 120 is removed with the noble metal 120-N filled the pores 112. Another wet metal etch or CMP process is carried out to further control height of the noble metal 120-N filling the pores. In FIG. 6, the aluminum oxide 115 and the residue aluminum film 115-AL at the bottom of the porous aluminum layer 115 are removed, then the noble metal rod array with the rod diameter d 120-N left with controlled height (H) and a well-defined nano-structured inter-pore distance (D) thus completing the fabrication of a noble metal nano-structured surface 100.

The geometries of the photolithographic masks applied in the above-described fabrication processes are designed to match the expected size of the sensing chip and the area of the metal pad, which locates at the corner of the chip. For field applications, the chemical detection sensing chips are formed as packaged sensing chips by applying different semiconductor packaging technologies, e.g., wire-bonding, flip-chips, system-on chip (SOC), etc., that will be further described in a different Patent Application.

As disclosed in FIGS. 1-6, this invention provides a novel method of using aluminum material and anodization method to creating nano-scaled porous structure on a silicon substrate with a conductive layer of metal coating or other compatible material surfaces. The layer thickness and the novel geometrical parameters of the nano-structure are precisely controllable because the processing parameters of the aluminum PVD, the anodization, and wet etch and the CMP processes are well known in the art. A precisely controllable wet oxide etching process is applied to remove the barrier layer at the bottom surface of the pores. The porous aluminum oxide layer is applied as a hard mask for depositing the noble metal into the pores 114 and then the residue aluminum film and the porous aluminum oxide are removed to expose the noble metal rods with well-controlled height H and distance D between the rods by controlling the anodizing processes on the aluminum layer or the CMP processes. The present invention thus provides a nano-structured surface fabricated by these novel processing steps on a silicon (100) substrate. By using the nano-structured surface, a Raman scattering band at 520 $cm^{-1}$ from silicon substrate is applied as the internal reference for calibrating spectrum frequency and intensity in the field application. A voltage may be applied to the nano-structure sensing surface through the conductive layer 110 for the purpose of attracting electrically charged trace chemical in the form of electrically charged molecular clusters, e.g., either negatively or positively charged particles depending on the sensing applications. Furthermore, the conductive layer 110 can also be cooled to a lower temperature below a normal room temperature to further enhance surface adsorption of molecules of interest.

Figure 7A:
FIGS. 7A to 7I are a series of cross sectional views and top views to show an alternate processing method to form nano-structure surface of this invention.
Figure 7D:
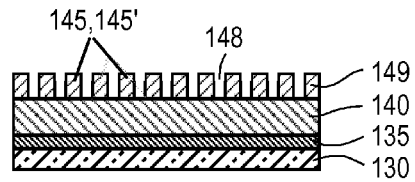
Figure 7B:
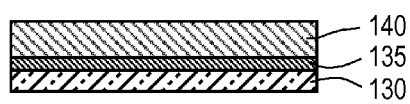
Figure 7G:
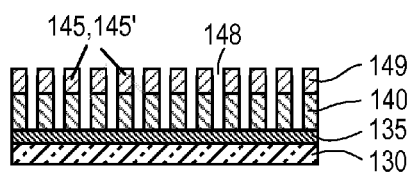
Figure 7C:
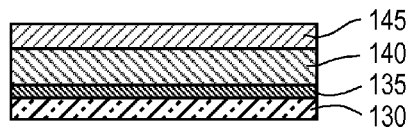

Referring to FIGS. 7A to 7F for a series of processing steps to fabricate another nano-structured noble metal surface of this invention, FIG. 7A shows a two-layer structure. The two-layer structure has an electrically and thermally conductive layer 135 deposited on top of a silicon substrate 130. In a preferred embodiment, the conductive layer 135 may be titanium (Ti) or nickel (Ni) layer. The substrate 130 may be a n-type silicon (100) flat wafer (3-8 Ω-cm) or oxidized (30-50 nm $SiO_2$) p-type silicon (100) flat wafers (5-10 mΩ-cm). The thickness of this conductive metal film 135 is usually controlled in the range of 100 Å-1,000 Å and optimized to provide best adhesion to a noble metal layer, e.g., a silver (Ag) layer, that will be subsequently deposited. The thickness of the metal layer 135 is also optimized for applying an electric bias to the sensing surface for trace chemical detection and further for applying a lower temperature to the sensing surface to enhance sensitivity of trace chemical detection. In FIG. 7B, a noble metal layer 140 is deposited on top of the conductive layer 135. The noble metal may be a silver layer, e.g., Ag layer having a thickness of 10-200 nm. In FIG. 7C, a second metal layer 145, e.g., an aluminum layer with a purity of 99.999% with a thickness in the range of 1.0-10.0 micrometers, is deposited on top of the noble metal layer 140.

Then an anneal operation is performed on the aluminum layer 145 at 400° C.-500° C. in a N₂ purged furnace for 2-5 hours to recrystallize the Al film.

Figure 7I:
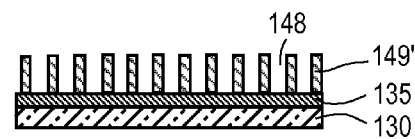

In FIG. 7D an anodization process is carried out to produce a porous structure in a form of porous aluminum oxide 145'. A top view is shown in FIG. 7E where the porous structure is formed with naturally self-assembled hexagon-shaped nano pore-array that includes a plurality of pores 148 surrounded by hexagon-shaped pore wall 149. After removing top anodized layer by a wet chemical process, a second anodization process is carried out to consume all Al metal so that the top porous Al₂O₃ layer 145' is right above the noble metal layer 140. Then a wet etch process is performed to widen the pores 148. As that shown in FIG. 7F, as the wet etch process proceeds, the pores 148 are widened and the walls 149 surrounding the pore become thinner. The etch process can be controlled to either form a plurality of nano-holes 148 surrounded by wall 149 or the pores 148 can be widened such that the pores 148 tangentially touch each other. The completion of the noble metal etch process through open hexagonal distributed pore array produces, a plurality of quasi-triangle columns 149' as a plurality of nano-rods.

Figure 7F:
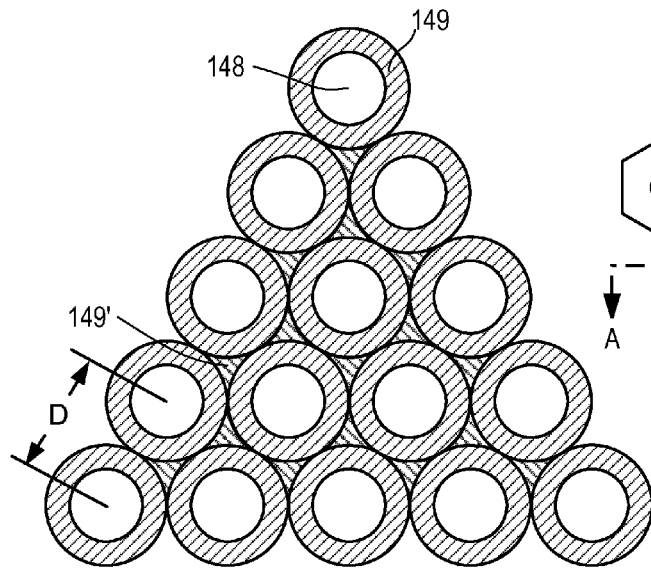
Figure 7E:
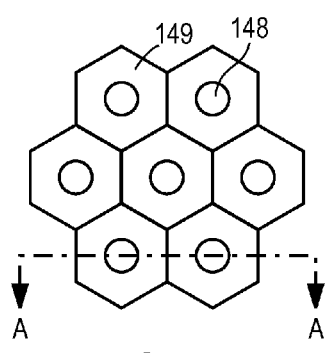
Figure 7H:
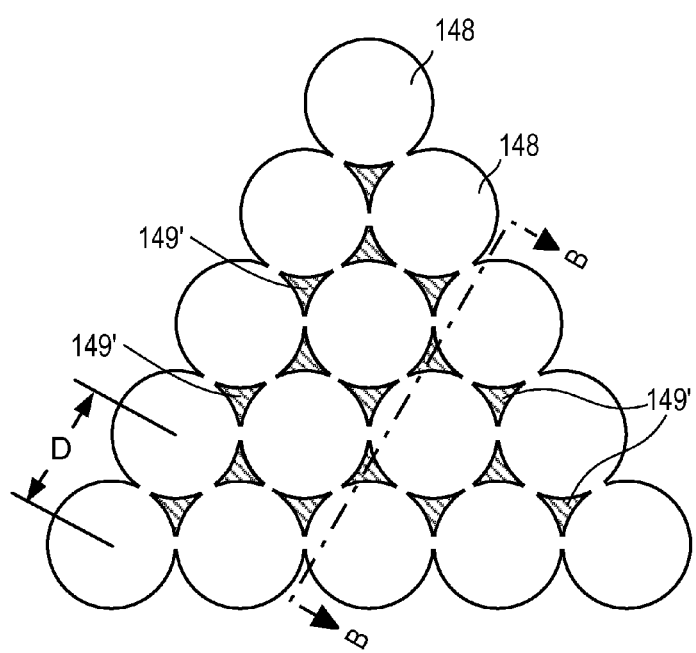

In FIGS. 7F and 7G, the noble metal layer 140 is etched down and the pores 148 are extended downward to reach the conductive titanium layer 135. In FIGS. 7H and 7I, a wet oxide etch is performed to remove the aluminum oxide followed by a wet metal etch to remove the aluminum residue at the bottom of the pores 148. The aluminum oxide 145' is removed from the top of the noble metal rod array 149' with controlled height (H), nano-rod diameter (d) and a well-defined nano-structured distance (D) between the rods thus completing the fabrication of a noble metal nano-structured surface 100 with quasi-triangle columns 149' distributed as a triangular array.

This method results in nano rods 149' with quasi-triangle shape. The coordination number is three. The advantages of this method over the embodiment shown in FIGS. 1 to 6 as that discussed above are i) better film adhesion between the Ti layer 135 and the Ag layer 140, ii) shorter inter-nano-rod distance, i.e., $D_A$ as shown in FIG. 7F, with about 40% reduction comparing to $D_B$ if all other process conditions are the same, iii) the height of the nano rods 149' can be well-controlled by Ag PVD within ±2% in film thickness variation through the whole wafer containing at least several hundred or even several thousand devices.

According to above descriptions, the self-assembled nano sensing surface is formed that the array of Ag triangle nano-rods 149' or a hexagonal array of nano-holes 148 wherein each Ag nano-rod or nano-hole is spatially isolated from each other.

The nano-rod array dimension size can be well controlled by processes mentioned above. Specifically, the array dimension and size are well controlled within the ranges as set forth below:

| | |
|---|---|
| 1) Ti film thickness: | 10-100 nm |
| 2) Nano rod diameter, d: | 5-300 nm |
| 3) Nano rod inter-particle distance, D: | 10-1000 nm |
| 4) Nano rod height, H: | 10-1000 nm |

On the other hand, the nano-hole array dimension and size can be well controlled by processes mentioned above. Specifically:

| | |
|---|---|
| 1) Ti film thickness: | 10-100 nm |
| 2) Nano hole diameter, d: | 5-300 nm |
| 3) Nano hole inter-hole distance, D: | 10-1000 nm |
| 4) Nano hole depth: | 10-1000 nm |

Figure 8:
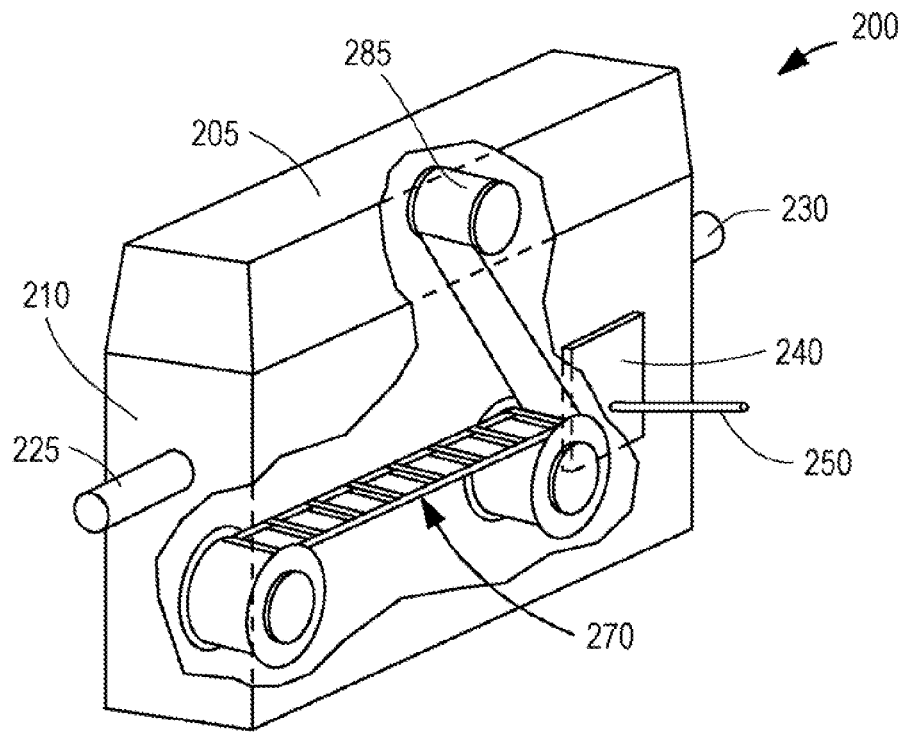
FIG. 8 is a perspective view for showing a SERS or SERRS probe contained in air tight sealed probe cell.

The nano-structured sensing surface provided with noble metallic nano-rods as shown in FIGS. 6 and 7H can be implemented to fabricate the probe cells as shown in FIG. 8. Referring to FIG. 8 for SERS or SERRS probe 200 of this invention implemented as a Raman scattering sensor, e.g., RamanSensor™. The probe 200 includes an airtight cell 210 covered by a housing cover 205. The airtight cell 210 encloses a mechanism 220 with further structure details shown in FIG. 9 below. The cell 210 includes an air outlet 225 connected to a vacuum pump (not shown) to generate a vacuum space inside the cell 210. The cell further includes an air inlet 230 that has a valve to intake sample molecules as sniff trace chemicals for adsorbing onto the nano-structured surface as will be further shown in FIG. 9. The probe 200 further includes a optical window 240 and a lens 250 for projecting laser beam as incident beam to strike on the nano-structured surface to generate a scattering signal to carry out a light scattering molecule detection operation. The airtight cell 210 thus provides an isolated space as a mini-environment for light scattering measurement.

Figure 9:
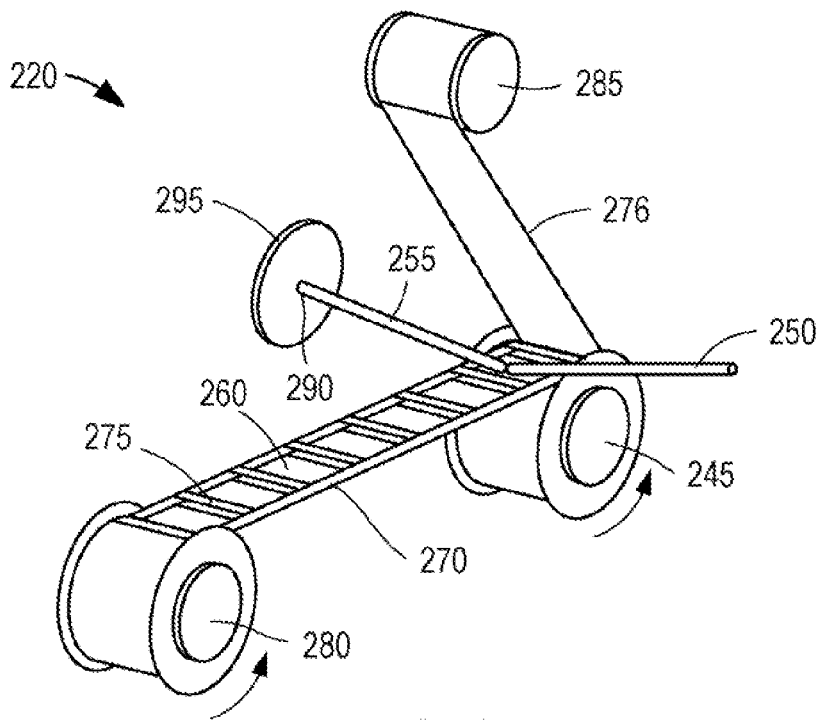
FIG. 9 is a perspective view for showing a roller for moving and exposing the nano-structured sensing surface to incident laser beam as implemented in a SERS or SERRS probe of FIG. 7

FIG. 9 is a perspective view of a mechanism 220 for supporting and operating the nano-structure surface that is fabricated with noble metal nano rods 120-N as shown in FIG. 6. The purpose of the nano-structured surface roller is to provide a mechanism to expose a fresh nano-structured surface, i.e., a RamanNanoChip™ surface 100, (one pocket size) to the air molecules inside the probe cell for any trace chemical to adsorb on the surface to provide surface enhanced Raman scattering when laser light strikes on the surface. In addition to the fabrication processes for a nano-structured surface 100 described above, the nano-structured surface 260 can be fabricated with photolithographic method, e-beam lithographic method, chemical reaction, PSL layer deposition followed by metal deposition, or special VLSI technology as described above. The nano-scaled noble metal particles are fabricated on a flexible metal foil or polymer material 270. To prevent the sensing surface from unexpected adsorbing molecules from air, the sensing surface is covered with a polymer or thin metal film 276. Further, to allow only a small portion of the surface to be exposed to intended sample molecules, the surface is structured such that each small area is surrounded with a circle, squared, rectangular, or any other type of shapes with sealing ridges 275. When a new measurement is to be made after sample molecules are pumped into the probe cell, the driving roller 280 and the thin film peel roller 285 will advance a distance equal to the sealed pocket size to peel off the thin film 276 cover and expose the fresh sensing surface 260 for molecules to adsorb onto it. The rollers 245, 280 rotate in the direction as shown by the arrows on the rollers 245, 280. The laser beam 250 enters the cell through an optical window and strikes the sensing surface 260. The reflected spectral light 255 is reflected off the exiting path by a reflecting mirror 290. The scattered light is collected by the objective lens 295.

Figure 10:
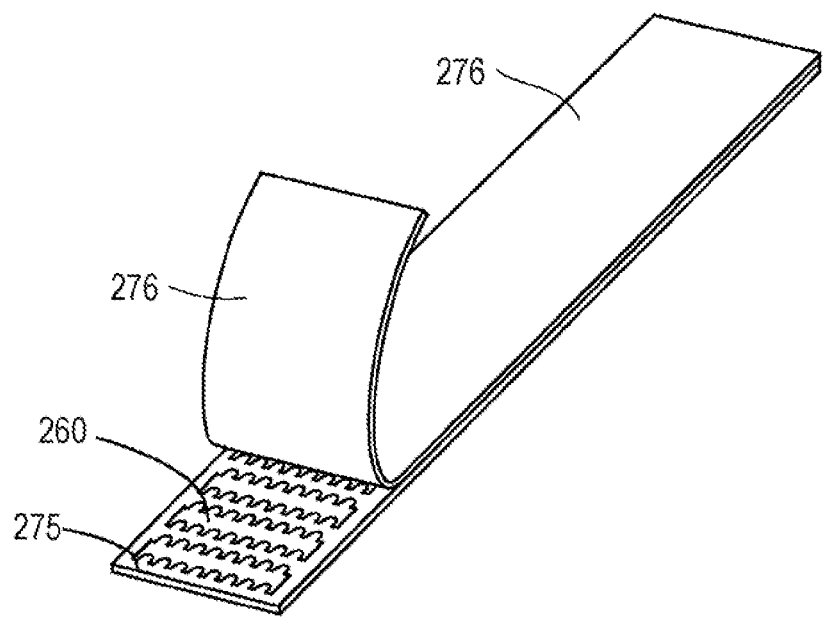
FIG. 10 is a perspective view for showing the surface packaging configuration of the nano-structured surface.

Referring to FIG. 10 for the structural details of the sealing ridges 275 surrounding and securing the nano-structured surface 260 in a pocket. In exposing the nano-structured surface 260 to the incident light 250, the thin film 276 is peeled off to allow the nano-structured sensing surface 260 to receive the incident laser beam and to allow interested trace chemicals adsorbed onto the fresh sensing surface to generate a Raman scattering light for chemical trace detection. The peeling-off configuration and sensing process enable the trace chemical detection operation to effectively minimize sample contamination and allow a new detection operation to conveniently carry out every trace chemical measurement by applying a fresh RamanNanoChip™.

Referring to FIGS. 9 and 10 again, the reflected laser beam 255 exits the probe cell through the exit window 240'. The scattered light also exits through the same exit window 240' with an angular distribution. A right-angled mirror 290 in the exiting laser beam path directs the beam away from its straight path and allows most of the scattering light to be collected by a following objective lens 295. The captured scattering light passes through following dispersing and imaging optics (not shown in the drawing) to form a spectrum on a CCD camera. To enhance the molecular adsorption of the metal surface, a DC voltage source is provided and connected to the sensing surface to provide a positive or negative voltage on the surface (not shown in the figures). Controlling the voltage can selectively enhance certain molecular adsorption; thus, provide a biased mechanism to enhance Raman scattering signals for certain molecules of interest. Furthermore, in order to enhance the molecular adsorption of nano-structured sensing surface, a thermoelectric cooler is applied to cool sensing surface down to the region from $0°$ C. to $20°$ C., which many trace chemicals of interest are condensed onto the sensing substrate in this temperature region, so that to further maximize trace chemical molecules to adsorb onto the sensing surface, and that further effectively enhance the Raman scattering signal.

To further enhance Raman scattering signal from a nano-structured sensing surface, a polarized laser beam is applied, which either close to parallel to the sensing surface and/or one of the principal axes of the nano array, or close to perpendicular to the sensing surface. The incident angle of the laser beam is arranged such that the laser polarization direction is closely aligned to the nano rods axis direction, i.e., perpendicular to the sensing surface normal direction, or parallel to the sensing surface. Since many organic chemical molecules are of benzene ring-like structure, such chemical molecules are expected to orient with its large ring structure that can be conveniently polarized for laying flatly on nano-rod edge surface, nano-rod top surface, or bottom surface between neighboring nano-rods.

To reduce Raman scattering noise, the voltage applied to the metal surface can be modulated with a known frequency to provide a mechanism for differential measurement. Several differential measurements techniques will be further described below.

Figure 11:
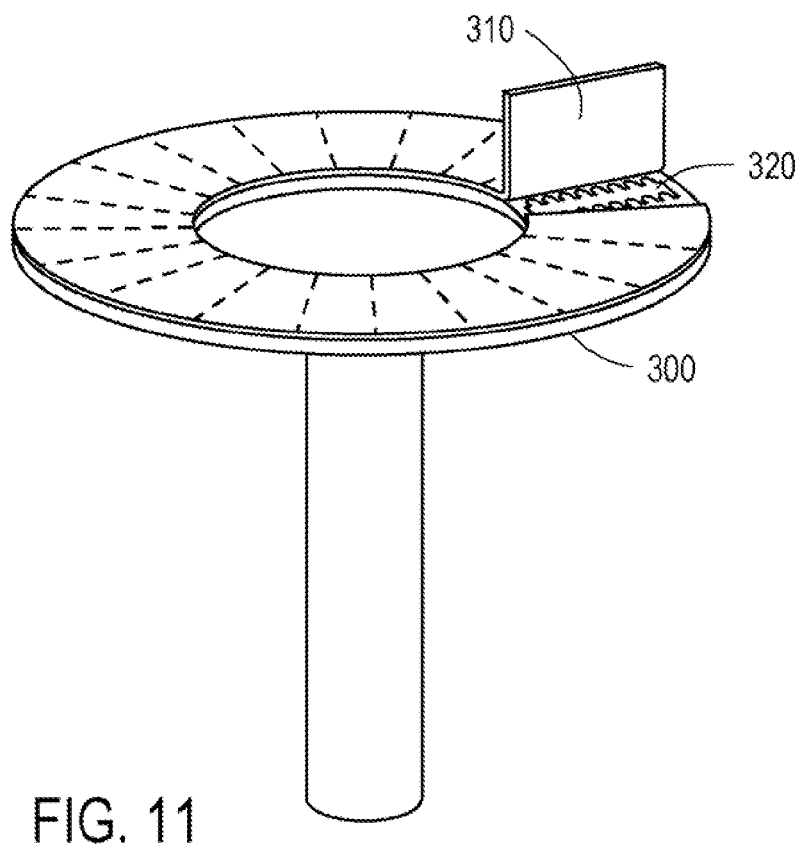
FIG. 11 is an alternate preferred embodiment with a nano-structured surface with pocket sealed and disposed as thin film on a rotary wheel.

An alternative embodiment of the nano-structured noble metal surface roller is illustrated in FIG. 11. In this embodiment, a rotary wheel 300 is constructed to provide pocket of nano-structured surface for SERS or SERRS. The wheel is motorized (not shown in the figure) and controlled by a electro-mechanical device. Each time sample air is pumped into the probe cell, the motorized wheel will rotate a step with the covering thin film 310 is lifted to expose the pocket surface 320. A number of pockets can be fabricated on the wheel to provide multiple measurements without changing any parts. Similar to the embodiment shown in FIG. 9, a DC voltage is connected to the metal surface to provide a positive or negative voltage for surface adsorption enhancement. The mechanism for exposing the nano-structured surface sealed in each individual pocket is similar to that of a roller driven one as described in previous paragraphs. The wheel 300 is enclosed inside the probe cell. The laser beam strikes the surface that is exposed to sample air and reflects off from the surface. As described above, the reflected spectral light is directed away from the light dispersing and collecting optics. Only the scattering light is dispersed and imaged to a CCD camera for spectral analysis.

The SERS or SERRS detector, e.g., RamanSensor™, as disclosed above has a compact size enclosed in an airtight probe cell with a nano-structured sensing surface, e.g., RamanNanoChip™, configured for individual exposure. The probe as disclosed can be conveniently deployed in the field. The nano-structured surface is configured and partitioned as pocketed and film protected surface for very cost effective and economical implementations. The nano-structured sensing surface is covered under the film and therefore is protected and free from contaminated particles before a trace chemical detection is performed. The ridges are effectively implemented to seal and securely attach the protective film onto the nano-structured surface to assure the nano-structured surface is free from contaminations. A mechanism is disclosed to lift the covering film to expose a small portion of the surface to sample and detect the molecules. The rollers as disclosed support and operate the nano-structured surface to expose only a single pocket at a time to control an accurate and effective operation of the detection processes. Also, the detection operation is performed with a continuously advanced fresh, uncontaminated surface for new SERS or SERRS measurement. The roller configuration further enhanced the film replacement process for more efficient chemical detection operations. The DC voltage as now applied to the nano-structured surface further enhances the adsorptions and sensitivity of trace chemical detection. In a preferred embodiment, the voltage applied to the conductive layer supports the nano-structured surface can be modulated to provide a differential signal to further reduce noises. To enhance the molecular adsorption of nano-structured sensing surface, a thermoelectric cooler is applied to cool sensing surface down to the region from $0°$ C. to $20°$ C., which many trace chemicals of interest are condensed onto the sensing substrate with higher probability in this temperature region. Furthermore, in order to enhance the molecular adsorption of nano-structured sensing surface, a polarized laser beam is applied, which either parallel to the sensing surface and/or one of the principal axes of the nano array, or perpendicular to the sensing surface.

According to FIGS. 1 to 11 and above descriptions, this invention discloses an optical sensor for detecting chemical molecules of interest. The optical scattering probe includes a nano-structured surface having a plurality of noble metal column or hole array disposed on top of a conductive layer. In a preferred embodiment, the optical scattering probe further includes a substrate supporting the nano-structured surface. In another preferred embodiment, each of noble metal column is disposed at about 10 to up to 1,000 nano-meters away from the neighboring noble metal columns. In another preferred embodiment, each of noble metal column is a silver metal column. In another preferred embodiment, the conductive layer further comprises a titanium layer. In another preferred embodiment, each the noble metal column having a quasi triangle shape. In another preferred embodiment, the conductive layer further comprising a titanium layer having a thickness of about one hundred to one thousand Angstroms. In another preferred embodiment, each the noble metal column having a cylindrical shape. In another preferred embodiment, each the noble metal column disposed as a hexagonal array. In another preferred embodiment, each the noble metal column disposed as a triangular array. In another preferred embodiment, each the noble metal column having a uniform height about ten to one thousand nanometers.

This invention further discloses a method for configuring a detector for detecting specific chemical molecules. The method for fabricating an optical scattering probe includes steps of A) depositing an conductive layer on a substrate followed by depositing an aluminum layer on top of the conductive layer. B) anodizing the aluminum layer to form a porous aluminum oxide layer having a plurality of pores. C) etching the plurality of pores through the aluminum layer. And D) filling the plurality of pores with a noble metal followed by removing a top layer of the noble metal and the aluminum oxide and the aluminum surrounding the noble metal in filling the pores to form a plurality of noble metal columns on top of the conductive layer. In a preferred embodiment, the step of depositing the conductive layer on the substrate is a step of depositing a titanium layer. In another preferred embodiment, the step of depositing the aluminum layer on top of the conductive layer is a step of depositing an aluminum layer with a purity of about 99.999%. In another preferred embodiment, the step of depositing the conductive layer on the substrate is a step of depositing a titanium layer having a thickness of about one hundred to one thousand Angstroms.

In addition to the regular trace chemical detections as described above, this invention further discloses additional methods of carrying out a chromatography operation e.g., gas chromatography (GC) or a high-performance liquid chromatography (HLPC) operation, before a trace chemical sensing is performed. A chromatography process is a process to separate a mixture by distribution of the components of the mixture between a mobile and a stationary phase over time. The mobile phase may be a liquid or gas phase and the stationary phase may be a component attached to a column packing material. This invention thus discloses a combined GC-Raman sensing system or a combined HPLC-Raman sensing system by first carrying out a classification by phase process, such as GC or HPLC, followed by detecting the trace chemicals by Raman scattering sensing process described above.

In addition to an electromagnetic effect, and a surface chemistry effect, the detection sensitivity of the Raman scattering sensors can also be enhanced by that the surface electron-photon coupling effect and surface interference effect can be combined with the dimension of the nano-structured surface. Specifically, the electron mean free path (MFP) on a gold or silver surface is about ten to fifty nano-meters as disclosed by Penn, D. R. in 1976 Phys. Rev. B13, 5248 and the Universal Curve (Physics at Surface, Andrew Zangwill, Cambridge University Press, 1988). The silver metal surface can be configured to have a nano-array with the scale to match the scale of the silver electron MFP. The physical properties of the silver nano-structured surface array demonstrate sudden significant changes when interacted with an incident visible polarized laser. The sudden changes of the physical properties can be quantified to correlate to the interaction between the photons and the electrons and other sub-atomic particles caused by the surface electron-photon coupling effect, surface interference effect, surface resonance effect, quasi-diffraction effect at the surface, and so on.

A MFP of an electron on a silver nano-structured surface is based on the Universal Curve as a function of the kinetic energy of that electron as tabulated below. Assuming the excited laser energy is transferred as kinetic energy to an electron on the Ag surface, the table below lists the MFP of the electron on a silver nano-structured surface for different laser wavelengths:

| a) laser wavelength = | 375 nm, MFP ≈ | 50 Å |
|---|---|---|
| b) | 532 nm | 100 Å |
| c) | 785 nm | 220 Å |
| d) | 1064 nm | 410 Å |

Accordingly, the electron MFP at the Ag metal surface is in the range of 5-50 nm under the condition that the excited laser wavelength is in the range of 375-1064 nm. From the above discussion, it can predict that the optimized and maximized SERS signal enhancement occurs under the condition that when the electron MFP is functionally matched by optimized several nano-structure parameters. These parameters include i) the diameter of the silver nano rod array or nano hole array d, ii) The inter-rod or the inter-hole distance on the nano-structured surface D, iii) the height of the nano rod array, or the depth of the nano hole array, or iv) any two of the above three parameters. The "functionally match" as described above may include the condition that Ag surface nano feature size(s) mentioned above is(are) approximately equal to, smaller than, integer numbers of, or with a special mathematical function to the estimated electron MFP or Ag metal. The functional match correlation can also be defined as by a functional relationship as characterized by the interaction between the photons and the electrons and other sub-atomic particles caused by the surface electron-photon coupling effect, surface interference effect, surface resonance effect, quasi-diffraction effect at the surface, an other inter-particle interactions.

Similarly above MFP of Ag electrons match Ag metal surface nano feature size(s) can be extended to i) The Electron Wavelength. Consider that the electron wavelength is in the range of about 2 Å-200 Å at the surface of Ag metal, if the metal surface nano feature size matches that range, then, non-conventional physical phenomena would occur under that laser beam excitation, such as surface enhanced Raman scattering, then resulted Raman scattering will get significant enhancement. ii) The Phonon Wavelength. Consider that the phonon wavelength is in the range of 2 Å-1,000 Å at the surface of Ag solid, if the metal surface nano feature size matches that range under the laser excitation, then resulted Raman scattering will get significant enhancement. Notice that the phonons are defined as the quanta of energy of the normal vibrational modes of a crystal lattice, and Raman spectrum records crystal lattice vibration. iii) The Phonon Free Mean Path. Consider that the phonon mean free path is in the range of about 2 Å-20 μm at the surface of Ag solid, if the metal surface nano feature size matches above range, then resulted Raman scattering will get significant enhancement. Notice that the phonons are defined as the quanta of energy of the normal vibrational modes of a crystal lattice, and Raman spectrum records crystal lattice vibration. Then Raman scattering can be significantly enhanced by the interaction among the photons, the electrons, the phonon, and other sub-atomic particles caused by the surface electron-photon-phonon coupling effect, surface electro-optical interference effect, surface resonance effect quasi-diffraction effect at the surface, an other inter-particle interactions.

Based on the above descriptions, considering the interaction between the incident laser and the nano-structured surface, the scattering sensing intensity can be further enhanced by applying the incident laser modulation to adjust the incident laser to have a glance incident angle such that the laser polarization direction is close to the direction of the nano-rod axis, i.e., perpendicular to the sensing surface or parallel to a sensing surface. The sensing performance can also be enhanced by shifting the wavelength of the excited laser with about half of Raman band width and applying a spectra difference analysis technique to filter out a large portion of the background noises or/and unwanted fluorescence signal from sample which both are with very broad band width. In addition to the above techniques, an alternate method is an electronic signal differential method to further enhance the performance of the scattering sensing process by shifting the charged-couple device (CCD) detection pixel position then applying a spectra difference method to reduce noises of detection.

According to above descriptions, this invention discloses a method for fabricating an optical scattering probe. The method includes A) depositing an conductive layer on a substrate followed by depositing an aluminum layer on top of the conductive layer; B) anodizing the aluminum layer to form a porous aluminum oxide layer having a plurality of pores; C) etching the plurality of pores through the aluminum layer; and D) filling the plurality of pores with a noble metal followed by removing a top layer of the noble metal and the aluminum oxide and the aluminum surrounding the noble metal in filling the pores to form a of noble metal columns on top of the conductive layer. In a preferred embodiment, the step of depositing the conductive layer on the substrate is a step of depositing a metal layer. In a preferred embodiment, the step of depositing the aluminum layer on top of the conductive layer is a step of depositing an aluminum layer with a purity of about 99.999%. In a preferred embodiment, the step of depositing the conductive layer on the substrate is a step of depositing a titanium layer having a thickness of about one hundred to one thousand Angstroms. In a preferred embodiment, the step of depositing the aluminum layer on top of the conductive layer is a step of depositing an aluminum layer having a thickness of about one to ten micrometers. In a preferred embodiment, the step of depositing the aluminum layer on top of the conductive layer further comprising a step of annealing and re-crystallizing the aluminum layer on top of the conductive layer supported on the substrate at an elevated temperature. In a preferred embodiment, the step of anodizing the aluminum layer to form a porous aluminum oxide layer having a plurality of pores is a step of forming a plurality of self-assembled array of pores each surrounded by a hexagon-shaped wall. In a preferred embodiment, the step of etching the pores through the aluminum layer further comprising a step of removing a top portion of the porous aluminum oxide layer for controlling a height of the pores. In a preferred embodiment, the method further includes a step of carrying out a second anodization following the step of etching the pores for removing the aluminum from a lower portion of the pores. In a preferred embodiment, the method further includes a step of carrying out an oxide etch following the step of second anodization for removing a barrier layer in the pores above the conductive layer for extending the pores to the conductive layer. In a preferred embodiment, the step of anodizing the aluminum layer to form a porous aluminum oxide layer having a plurality of pores is a step of controlling a diameter and a distribution of the pores by controlling processing parameters of anodizing the aluminum layer and etching the pores. In a preferred embodiment, the step of filling the plurality of pores with a noble metal is a step of filling the pores with noble metal, such as silver (Ag), gold (Au) or copper (Cu). In a preferred embodiment, the step of filling the plurality of pores with a noble metal followed by removing a top layer of the noble metal is a step of applying a chemical-mechanical planarization (CMP) process for controlling a height of the pores. In a preferred embodiment, the step of filling the plurality of pores with a noble metal followed by removing a top layer of the noble metal and the aluminum oxide and the aluminum surrounding the noble metal is a step of applying a wet etch process for controlling a height of the noble metal columns. In a preferred embodiment, the method further includes a step of applying a voltage to the conductive layer. In a preferred embodiment, the method further includes step of applying a low temperature to the conductive layer. In a preferred embodiment, the method further includes a step of packaging the substrate supporting the plurality of noble metal columns into a trace chemical detecting chip. In a preferred embodiment, the method further includes a step of placing an array of the trace-chemical detecting chips into a moveable surface for sequentially applying each of the detecting chip as an optical scattering probe. In a preferred embodiment, the method further includes a step of mounting the moveable surface on a rotational wheel for sequentially applying each of the detecting chip as an optical scattering probe. In a preferred embodiment the method further includes a step of covering the detecting chip with a removable protective film for applying the detection chip as an uncontaminated detection chip.

This invention further discloses a method for fabricating an optical scattering probe. The method includes steps of A) depositing an conductive layer on a substrate followed by depositing a noble metal layer on top of the conductive layer and then an aluminum layer on top the noble metal layer; B) anodizing the aluminum layer to form a porous aluminum oxide layer having a plurality of pores; and C) etching the plurality of pores through the aluminum oxide layer and the noble metal layer for forming a nano-hole array. In a preferred embodiment, the step of etching the plurality of pores through the aluminum oxide layer and the noble metal layer further comprising a step of widening the pores followed by removing the aluminum oxide layer for forming a plurality of noble metal column on top of the conductive layer. In a preferred embodiment, the step of depositing the conductive layer on the substrate is a step of depositing a metal layer, such as titanium (Ti), nickel (Ni), and so on. In a preferred embodiment, the step of depositing the aluminum layer on top of the noble metal layer is a step of depositing an aluminum layer with a purity of about 99.999%. In a preferred embodiment, the step of depositing the conductive layer on the substrate is a step of depositing a titanium layer having a thickness of about one hundred to one thousand Angstroms. In a preferred embodiment, the step of depositing the aluminum layer on top of the noble metal layer is a step of depositing an aluminum layer having a thickness of about one to ten micrometers. In a preferred embodiment, the step of depositing the aluminum layer on top of the noble layer further comprising a step of annealing and re-crystallizing the aluminum layer on top of the noble metal layer over the conductive layer supported on the substrate at an elevated temperature. In a preferred embodiment, the step of anodizing the aluminum layer to form a porous aluminum oxide layer having a plurality of pores is a step of forming a plurality of self-assembled array of pores each surrounded by a hexagon-shaped wall. In a preferred embodiment, the step of etching the pores through the aluminum layer and the noble metal layer further comprising a step of carrying out a second anodization for removing aluminum oxide layer followed by a second etch for removing a top portion of the noble metal layer. In a preferred embodiment, the step of removing the aluminum oxide layer for forming a plurality of noble metal column on top of the conductive layer further comprises a step of removing a top portion of the noble metal layer for controlling a height of the noble metal columns. In a preferred embodiment, the step of etching and widening the plurality of pores further comprising a step of widening the pores whereby the pores tangentially touching each other to form a plurality of quasi triangular noble metal columns. In a preferred embodiment, the step of anodizing the aluminum layer to form a porous aluminum oxide layer having a plurality of pores is a step of controlling a diameter and a distribution of the pores by controlling processing parameters of anodizing the aluminum layer and etching the pores. In a preferred embodiment, the step of form a noble metal layer on top of the conductive layer a step of forming a noble metal layer, such as Ag, Au, or Cu, etc. In a preferred embodiment, the step of forming the noble metal layer further comprising a step of applying a chemical-mechanical planarization (CMP) process for controlling a height of the noble metal layer. In a preferred embodiment, the step of removing the aluminum oxide layer and a top portion of the noble metal layer further comprising a step of applying a wet etch process for controlling a height of the noble metal columns. In a preferred embodiment, the method further includes a step of applying a voltage to the conductive layer. In a preferred embodiment, the method further includes a step of applying a low temperature to the conductive layer. In a preferred embodiment, the method further includes a step of packaging the substrate supporting the plurality of noble metal columns into a trace chemical detecting chip. In a preferred embodiment, the method further includes a step of placing an array of the trace chemical sensing chips into a moveable surface for sequentially applying each of the sensing chip as an optical scattering probe. In a preferred embodiment, the method further includes a step of mounting the moveable surface on a rotational wheel for sequentially applying each of the sensing chip as an optical scattering probe. In a preferred embodiment, the method further includes a step of covering the detecting chip with a removable protective film for applying the detection chip as an uncontaminated detection chip.

This invention further discloses an optical scattering probe that includes a nano-structured surface having a plurality of noble metal columns disposed on top of a conductive layer. In a preferred embodiment, the probe further includes a substrate supporting the nano-structured surface. In a preferred embodiment, each of noble metal columns is disposed at 10 to 1000 nanometers away from neighboring noble metal columns. In a preferred embodiment, each of noble metal columns is a silver (Ag), gold (Au), or copper (Cu) metal column. In a preferred embodiment, the conductive layer further includes a titanium or nickel layer. In a preferred embodiment, each the noble metal columns having a quasi-triangle shape. In a preferred embodiment, the conductive layer further comprising a titanium layer having a thickness of about one hundred to one thousand Angstroms. In a preferred embodiment, each the noble metal columns have a cylindrical shape. In a preferred embodiment, each of the noble metal columns disposed as a hexagonal array. In a preferred embodiment, each of the noble metal columns disposed as a triangular array. In a preferred embodiment, each of the noble metal columns has a uniform height about ten to two hundred nanometers. In a preferred embodiment, the probe further includes a voltage source for applying a voltage to the conductive layer. In a preferred embodiment, the probe further includes a cooler for lowering a temperature of the conductive layer. In a preferred embodiment, the probe further includes a package packaging the substrate supporting the plurality of noble metal columns into a trace chemical detecting chip. In a preferred embodiment, the probe further includes a movable surface for placing an array of the trace-chemical detecting chips for sequentially applying each of the detecting chip as an optical scattering probe. In a preferred embodiment, the probe further includes a rotational wheel for mounting the movable surface for sequentially applying each of the detecting chip as an optical scattering probe. In a preferred embodiment, the probe further includes a removable protective film for covering the detecting chip for applying the detection chip as an uncontaminated detection chip.

This invention further discloses a method for forming a nano-structure that includes steps of applying an anodization process for forming a porous layer having a plurality of holes followed by etching a plurality of nano-holes. In a preferred embodiment, the method further includes filling the nano-holes with a nano-column material followed by removing the porous layer for forming a plurality of nano-columns. In another preferred embodiment, the step of forming the porous layer is a step of forming the porous layer on top of a layer composed of a nano-column material followed by etching and widening the nano-holes to form a plurality of nano-columns.

This invention further discloses a trace chemical detection system that includes a chromatography system for separating components of mixture by distribution of the components in different phases. The system further includes a Raman scattering probe for detecting a trace chemical wherein the Raman-scattering probe further includes a nano-structured surface having a plurality of noble metal columns disposed on top of a conductive layer.

This invention further discloses a trace chemical detection system that includes a Raman scattering probe includes a nano-structured surface having a plurality of noble metal columns disposed on top of a conductive layer. The system further includes a nano structured noble metal sensing surface has a nano feature size functionally matched with one of or combination among following physical parameters: i) an electron mean-free-path (MFP) of the electrons on a surface of the noble metal, in the range of 0.2-100 nm, or/and ii) an electron wavelength of the electrons on a surface of the noble metal, in the range of 0.2-20 nm, or/and iii) a phonon mean-free-path (MFP) of the phonons on a surface of the noble metal in the range of 0.2 nm-20 µm, or and iv) a phonon wavelength of the phonons on a surface of the noble metal in the range of 0.2-100 nm, under the condition that the photon energy of the adjusted incident laser transfers to surface electron kinetic energy of noble metal. The sensing performance can also be enhanced by shifting the wavelength of the excited laser with about half of Raman band width and applying a spectra difference analysis technique to filter out a large portion of the background noises or/and unwanted fluorescence signal from sample which both are with very broad band width. In addition to the above techniques, an alternate method is an electronic signal differential method, by shifting the charged-couple device (CCD) detection pixel position then applying a spectra difference method may also be useful to reduce noises and further enhance the performance of the scattering sensing process.

This invention further discloses a trace chemical detection system that includes a Raman-scattering probe includes a nano-structured surface having a plurality of noble metal columns disposed on top of a conductive layer. The system further includes an incident laser controller for controlling a modulation and polarization of the incident laser for optimizing a detection of a trace chemical. In a preferred embodiment, the system further includes a Raman band at 520 $cm^{-1}$ from a silicon crystalline substrate and that is applied as internal reference standard for Raman system frequency and intensity calibration.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

We claim:

1. A method for fabricating a Raman scattering probe, comprising:
   forming a noble metal layer over a substrate, wherein the noble metal layer comprises a noble metallic material;
   forming an array of pores in the noble metal layer, wherein adjacent pores are separated by walls made of the noble metallic material, wherein the array of pores is substantially in the form of a hexagonal array;
   removing portions of the noble metallic material in the walls between adjacent pores to connect adjacent pores; and
   forming an array of substantially triangular-shaped columns over the substrate to form the Raman scattering probe,
   wherein each of the substantially triangular-shaped columns is defined by three adjacent pores that are tangentially connected in the step of removing portions of the noble metallic material in the walls between adjacent pores;
   wherein distances between adjacent substantially triangular-shaped columns are from about 10 nm to about 1000 nm, and
   wherein the substantially triangular-shaped columns comprise the noble metallic material.

2. The method of claim 1, wherein the substantially triangular-shaped columns have widths in a range from about 5 nm to about 300 nm.

3. The method of claim 1, wherein the substantially triangular-shaped columns have heights in a range from about 10 nm to about 1000 nm.

4. The method of claim 1, wherein of the array of pores have diameters in a range from about 5 nm to about 50 nm after the step of forming an array of pores.

5. The method of claim 1, further comprising:
   forming an upper layer on the noble metal layer;
   forming the array of pores through the upper layer and in the noble metal layer; and
   removing the upper layer after the step of forming an array of pores in the noble metal layer.

6. The method of claim 5, wherein the upper layer comprises aluminum, wherein the step of forming the array of pores through the upper layer comprises anodizing at least a portion of the aluminum to form aluminum oxide in the upper layer.

7. The method of claim 5, wherein the upper layer has a thickness from about 1 micron to about 10 micron.

8. The method of claim 1, wherein the array of pores is formed by self-assembly.

9. The method of claim 1, wherein the array of columns is substantially in the form of a triangular array.

10. The method of claim 1, wherein the noble metal layer comprises at least one of Ag, or Au.

11. The method of claim 1, wherein the columns are substantially perpendicular to the substrate.

12. The method of claim 1, wherein the step of removing portions of the noble metallic material in the walls between adjacent pores comprises etching the noble metallic material in the walls to widen the pores.

13. The method of claim 1, further comprising: forming an adhesion layer on a substrate, wherein the noble metal layer is formed on the adhesion layer.

14. The method of claim 13, wherein the adhesion layer comprises Ti or Ni.

15. The method of claim 13, wherein the adhesion layer has a thickness from about 100 Angstroms to about 1000 Angstroms.

16. A method for fabricating a Raman scattering probe, comprising:
   forming a noble metal layer comprising a first material over a substrate;
   forming an upper layer comprising a second material on the noble metal layer;
   forming the array of pores through the upper layer, wherein at least one of the plurality of pores forms a hexagonal shape;
   extending the array of pores in the noble metal layer, wherein adjacent pores are separated by walls made of the first material and the second material;
   removing the first material and the second material in the walls between adjacent pores to connect adjacent pores;
   forming an array of substantially triangular-shaped columns over the substrate;
   wherein each of the substantially triangular-shaped columns is defined by three adjacent pores that are tangentially connected in the step of removing portions of removing the first material and the second material in the walls between adjacent pores; and
   removing the second material in the array of substantially triangular-shaped columns to form the Raman scattering probe, wherein distances between adjacent substantially triangular-shaped columns are from about 10 nm to about 1000 nm, wherein the substantially triangular-shaped columns have widths in a range from about 5 nm to about 300 nm.

17. The method of claim 16, wherein the array of substantially triangular-shaped columns comprises substantially the first material after the step of removing the second material in the array of substantially triangular-shaped columns.

18. The method of claim 16, wherein the substantially triangular-shaped columns have heights in a range from about 10 nm to about 1000 nm.

19. The method of claim 16, wherein of the array of pores have diameters in a range from about 5 nm to about 50 nm after the step of extending.

20. The method of claim 16, wherein the upper layer comprises aluminum, wherein the step of forming the array of pores through the upper layer comprises anodizing at least a portion of the aluminum to form aluminum oxide in the upper layer.

21. The method of claim 16, wherein the upper layer has a thickness from about 1 micron to about 10 micron.

22. The method of claim 16, wherein the array of pores is substantially in the form of a hexagonal array.

23. The method of claim 16, wherein the array of columns is substantially in the form of a triangular array.

24. The method of claim 16, wherein the first material comprises at least one of Ag, or Au.

25. The method of claim 16, wherein the columns are substantially perpendicular to the substrate.

26. The method of claim 16, wherein the step of removing the first material and the second material in the walls between adjacent pores comprises etching the first material and the second material in the walls to widen the pores.

27. The method of claim 16, further comprising: forming an adhesion layer on a substrate, wherein the noble metal layer is formed on the adhesion layer.

28. The method of claim 27, wherein the adhesion layer comprises Ti or Ni.

29. The method of claim 27, wherein the adhesion layer has a thickness from about 100 Angstroms to about 1000 Angstroms.

30. A method for fabricating a Raman scattering probe, comprising:
  forming an array of pores in a noble metal layer comprising a noble metallic material over a substrate, wherein adjacent pores are separated by walls made of the noble metallic material, wherein at least one of the plurality of pores forms a hexagonal shape;
  removing the noble metallic material in the walls between adjacent pores to connect adjacent pores;
  forming an array of substantially triangular-shaped columns over the substrate to form the Raman scattering probe, wherein each of the substantially triangular-shaped columns is defined by three adjacent pores that are tangentially connected in the step of removing the noble metallic material in the walls between adjacent pores; and wherein distances between adjacent substantially triangular-shaped columns are from about 10 nm to about 1000 nm, wherein the substantially triangular-shaped columns have widths in a range from about 5 nm to about 300 nm; and
  absorbing molecules of a trace chemical to surfaces of the substantially triangular-shaped columns on the Raman scattering probe, wherein the molecules adsorbed to the surfaces of the substantially triangular-shaped columns are configured to scatter an incident laser beam illuminating the Raman scattering probe to produce scattered light.

31. The method of claim 30, further comprising applying a bias voltage to the noble metal layer when the molecules adsorbed to the surfaces of the substantially triangular-shaped columns scatter the incident laser beam to produce the scattered light.

32. The method of claim 30, further comprising cooling the noble metal layer when the molecules adsorbed to the surfaces of the substantially triangular-shaped columns scatter the incident laser beam to produce the scattered light.

33. The method of claim 30, further comprising introducing a liquid or a gas comprising the molecules of the trace chemical to contact with the surfaces of the substantially triangular-shaped columns.

34. The method of claim 30, wherein the substantially triangular-shaped columns have heights in a range from about 10 nm to about 1000 nm.

35. The method of claim 30, wherein the noble metallic material comprises at least one of Ag, or Au.

36. The method of claim 30, wherein the columns are substantially perpendicular to the substrate.

37. The method of claim 30, wherein the step of removing the noble metallic material in the walls between adjacent pores comprises etching the noble metallic material in the walls to widen the pores.

38. The method of claim 30, further comprising: forming an adhesion layer on a substrate, wherein the noble metal layer is formed on the adhesion layer.

39. The method of claim 38, wherein the adhesion layer comprises Ti or Ni.

40. The method of claim 38, wherein the adhesion layer has a thickness from about 100 Angstroms to about 1000 Angstroms.

* * * * *